United States Patent
Moriyoshi et al.

(10) Patent No.: US 6,887,992 B2
(45) Date of Patent: May 3, 2005

(54) 3-CEPHEM DERIVATIVE CRYSTAL

(75) Inventors: Takashi Moriyoshi, Tokushima (JP);
Yasuhiro Uosaki, Tokushima (JP);
Yutaka Kameyama, Tokushima (JP);
Daisuke Suzuki, Tokushima (JP);
Yoshiko Seo, Tokushima (JP)

(73) Assignee: Otsuka Kagaku Kabushiki Kaisha, Osaka (JP)

( * ) Notice: Subject to any disclaimer, the term of this patent is extended or adjusted under 35 U.S.C. 154(b) by 0 days.

(21) Appl. No.: 10/679,451

(22) Filed: Oct. 7, 2003

(65) Prior Publication Data

US 2004/0073023 A1 Apr. 15, 2004

Related U.S. Application Data

(62) Division of application No. 10/089,194, filed as application No. PCT/JP00/06693 on Sep. 28, 2000.

(30) Foreign Application Priority Data

Sep. 30, 1999 (JP) ............................................. 11-278535
Sep. 30, 1999 (JP) ............................................. 11-279080

(51) Int. Cl.⁷ .......................................... C07D 501/30
(52) U.S. Cl. ..................................................... 540/215
(58) Field of Search ........................................ 540/215

(56) References Cited

U.S. PATENT DOCUMENTS 3,925,372 A * 12/1975 Chauvette .................. 540/215
4,581,166 A   4/1986 Peter et al. ............... 260/112.5
4,694,079 A * 9/1987 Crast, Jr. .................... 540/215
5,707,634 A * 1/1998 Schmitt ...................... 424/400
5,998,610 A * 12/1999 Centellas et al. ........... 540/215
6,221,153 B1 * 4/2001 Castor et al. ................. 117/11
6,552,185 B1 * 4/2003 Boogers et al. ............. 540/220
2002/0128254 A1 * 9/2002 Kawamoto et al. ..... 514/210.13

FOREIGN PATENT DOCUMENTS

| EP | 0 126 351 A | 5/1984 |
| EP | 0 126 351 A1 | 5/1984 |
| EP | 0 319 019 A2 | 12/1988 |
| EP | 0 638 573 A | 2/1995 |
| GB | 1356437 | 6/1974 |
| WO | WO 95/07283 | 3/1995 |

OTHER PUBLICATIONS

Patent Abstract of Japan, Publication No. 63045284 A, Publication Date Feb. 26, 1988.

Tanaka, Hideo et al.; "Aerobic Oxidation of 3–Iodomethyl–$\Delta^3$–cephem–4–carboxylate to 3–Formyl–$\Delta^3$–cephem–4–carboxylate through 3–Hydroperoxymethyl–$\Delta^3$–cephem–4–carboxylate"; *Bull. Chem. Soc. Jpn.*; vol. 69, No. 1, pp. 229–233; 1996.

* cited by examiner

Primary Examiner—Mark L. Berch
(74) Attorney, Agent, or Firm—Kubovcik & Kubovcik

(57) ABSTRACT

A 3-cephem derivative crystal which is a clathrate compound comprising p-methoxybenzyl ester of 7-phenylacetamide-3-formyl-3-cephem-4-carboxylic acid and dimethylformamide and a process for preparing the 3-cephem derivative crystal.

2 Claims, 1 Drawing Sheet

3-CEPHEM DERIVATIVE CRYSTAL

This application is a division of application Ser. No. 10/089,194, filed Mar. 27, 2002 now abandoned, which is a 371 of PCT/JP00/06693, filed Sep. 28, 2000.

TECHNICAL FIELD

The present invention relates to a 3-cephem derivative in crystalline form which can be prepared by a novel crystallization method, the 3-cephem derivative being useful as an intermediate or a final product of pharmaceuticals such as cefixime, ceftibuten and cefdinir (Katsuharu SAKAI, "Handbook of Recent Antibiotics", p.p.83, 85 and 86) which are currently widely used as pharmaceutical antibiotics, and a process for preparing the same.

BACKGROUND ART

Generally employed for crystallizing 3-cephem derivatives are crystallization methods using a combination of a good solvent which is superior in the power of dissolving the substrate and a poor solvent which is inferior in the power of dissolving the substrate.

However, these conventional crystallization methods have the following defect. The poor solvent partly becomes highly concentrated in the crystallization system when the poor solvent is dispersed in the good solvent, so that an amorphous powder is produced in most cases without formation of crystalline nucleus because of abrupt deposition occurring in the part. In addition, the obtained 3-cephem derivative is very unlikely to have enhanced purity because it generally contains impurities.

The amorphous powder, compared with crystalline powder, tends to raise troubles such as leakage and clogging in filter cloth and thus a significantly prolonged time for filtration, and reduction of purity due to insufficient washing. Conventional methods for crystallizing 3-cephem derivatives generally involve an increased loss of filtrate under mild conditions approximately at room temperature and fail to give the contemplated product in a sufficient yield because of marked temperature dependency of substrate solubility in the solvent used.

Since 3-cephem derivatives have a high affinity for organic solvents, conventional crystallization methods using a large amount of organic solvent increase the adsorption quantity of organic solvent, making it very difficult in most cases to remove the remaining solvent by drying. Further, an amorphous powder of 3-cephem derivative is generally low in heat stability and thus entails difficulty in drying at high temperatures, necessitating drying under a high vacuum. For this reason, conventional crystallization methods give only amorphous powders. In the foregoing situation, there is an ardent demand for a novel method for crsytallization of 3-cephem derivatives.

On the other hand, attempts have been reportedly made to develop a new crystallization technology using carbon dioxide in a supercritical state as a poor solvent [Chemical Engineering Symposium Series: Vol.49, p.p.200 to 205 (1995), Idemitsu Giho: Vol.35, No.5, p.p.600 to 606 (1992), etc.]. These reports describe crystallization techniques for converting stable substances which are inherently crystalline, suggesting nothing on the possibility of crystallizing unstable compounds such as those which can be made into only an amorphous powder by conventional methods.

An object of the present invention is to provide a novel process for preparing crystals which process can produce a high-purity 3-cephem derivative in crystalline form from an amorphous powder or oil of a 3-cephem derivative whose stability is very important.

DISCLOSURE OF THE INVENTION

The present invention provides a process for preparing 3-cephem derivative crystals, the process comprising crystallizing a 3-cephem derivative in the form of amorphous powder or oil using a good solvent, and a poor solvent comprising carbon dioxide in a supercritical or subcritical state to give a 3-cephem derivative in crystalline form.

The invention provides a process for preparing 3-cephem derivative crystals, the process comprising introducing carbon dioxide in a supercritical or subcritical state under increased pressure into a reaction mixture in a procedure for preparing a 3-cephem derivative to give a 3-cephem derivative in crystalline form.

The invention also provides a process for preparing 3-cephem derivative crystals, the process comprising introducing a reaction mixture in a procedure for preparing a 3-cephem derivative into carbon dioxide in a supercritical or subcritical state under increased pressure to give a 3-cephem derivative in crystalline form.

The invention further provides 3-cephem derivative crystals which are clathrate compounds comprising p-methoxybenzyl ester of 7-phenylacetamide-3-formyl-3-cephem-4-carboxylic acid and dimethylformamide.

The present inventors directed attention to the facts that carbon dioxide in a supercritical or subcritical state is highly permeable and diffusible, and at the same time can form a strong cluster with an organic compound (substrate), and also to the fact that it can control the solubility of an organic compound (substrate) only by slight change of pressure and temperature.

More specifically, it was presumed that when used as a poor solvent, carbon dioxide in a supercritical or subcritical state is quickly homogeneously permeated and diffused into a good solvent having the substrate dissolved therein due to its high permeability and diffusibility and can simultaneously form a cluster with a 3-cephem derivative. As a result, each of 3-cephem derivatives becomes to exist in closer intermolecular distance and is facilitated to form a crystalline lattice.

The inventors investigated methods of poor solvent crystallization of a 3-cephem derivative using carbon dioxide in a supercritical or subcritical state as a poor solvent, while employing various combinations of good solvents, temperatures, pressures and the like with the result that a high-purity 3-cephem derivative in crystalline form was successfully produced in a high yield from an amorphous powder or oil of 3-cephem derivative.

The crystals thus obtained were found to have a high purity and a high stability. It was further discovered that the reaction mixture can be used in place of the solution of 3-cephem derivative in a good solvent. Namely the contemplated 3-cephem derivative in crystalline form can be directly obtained with a high purity. Furthermore, since carbon dioxide which takes a gaseous form at atmospheric pressure is used as a poor solvent, dry crystals substantially not containing the residual solvent can be easily produced merely by bringing the obtained crystals to atmospheric pressure.

In this way, the inventors developed a new crystallization method using carbon dioxide in a supercritical or subcritical state as a poor solvent. Thereby high-purity, highly stable crystals without residual solvent can be produced in a high yield by facilitated isolation and purification. Thus, the present invention was completed.

Crystals formed of 3-cephem derivative alone can be usually produced. Depending on a combination of a 3-cephem derivative and a good solvent, a clathrate compound may be produced. The invention includes the clathrate compound. For example, when using p-methoxybenzyl ester of 7-phenylacetamide-3-formyl-3-cephem-4-carboxylic acid [3-formylcephem compound (1)] as a 3-cephem derivative and dimethylformamide (DMF) as a good solvent, a clathrate compound comprising them can be produced. The term "clathrate compound" used herein refers to a compound wherein when crystals have two kinds of molecules combined under proper conditions, one kind of molecules have a structure in the form of a tunnel, a layer, a network or the like while the other kind of molecules are present in a clearance (open space) of the structure.

P-methoxybenzyl ester of 7-phenylacetamide-3-formyl-3-cephem-4-carboxylic acid of the formula (1) given below (which is hereinafter referred to as "3-formylcephem compound (1)" unless specifically indicated) possesses a highly reactive formyl group in the molecule, and can be easily made into various kinds of alkenylcephem compounds on reaction with an ylide compounds (wittig reaction). Consequently the 3-formylcephem compound (1) is very useful as an intermediate in the synthesis of cefixime (Katsuharu SAKAI, "Handbook of Recent Antibiotics", 10th ed., p.83) which is widely used today as an antibiotic.

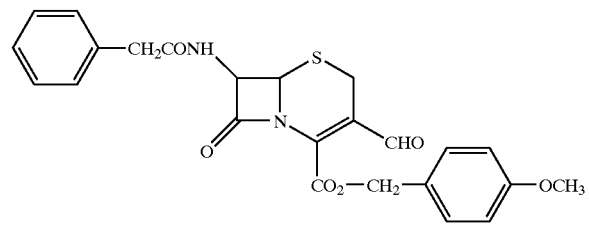

(1)

The 3-formylcephem compound (1) is prepared as an oil or amorphous powder, for example, by producing p-methoxybenzyl ester of 7-phenylacetamide-3-chloromethylcephem-4-carboxylic acid according to the method disclosed in Tetrahedron Lett., 23, 2187 (1982); reacting the ester with potassium iodide to substitute a chlorine atom in the ester with an iodine atom, giving p-methoxybenzyl ester of 7-phenylacetamide-3-iodomethylcephem-4-carboxylic acid; and oxidizing the same with oxygen according to the methods described in Synlett., 660 (1990), JP-A-3-258783, etc.

The 3-formylcephem compound (1) has the following property. When assuming the form of a solution, oil or amorphous powder, the compound (1) is likely to cause decomposition reaction by air oxidation of formyl group (Test Example 1). For this reason, the contemplated antibiotic can not be prepared with a high purity in a high yield because of the decomposition of the compound (1) in an industrial-scale manufacture of antibiotics such as cefixime from the 3-formylcephem compound (1). Even if the oil or amorphous powder is crystallized by conventional crystallization methods, e.g. using a poor solvent for reducing the degree of decomposition, no crystal can grow or other than amorphous powder can not be obtained (Reference Example 2).

There has been an ardent desire for crystals of 3-formylcephem compound (1) which are stable and highly pure without entailing decomposition for a long time.

The invention can provide crystals of 3-formylcephem compound (1) which are stable and free of decomposition while retaining its inherent high reactivity.

According to the invention, there can be obtained clathrate crystals including crystals of stable and high-purity 3-formylcephem compound (1) when a crystallization method is carried out using supercritical or subcritical carbon dioxide in dimethylformamide for crystallization of oil or amorphous powder of 3-formylcephem compound (1).

In addition, the invention provides a process for preparing crystals of 3-cephem derivative, the process comprising the steps of dissolving an amorphous powder or oil of 3-cephem derivative in a good solvent and conducting a crystallizing procedure using as a seed crystal the crystals obtained by the process as defined in claim 1.

When crystals of 3-cephem derivative are once obtained, e.g. by the crystallization method using, as a poor solvent, carbon dioxide in a supercritical or subcritical state according to the process of claim 1 as defined above, crystals of 3-cephem derivative can be prepared easily from an amorphous powder or oil of 3-cephem derivative without use of carbon dioxide in a supercritical or subcritical state in the ensuing procedure. High-purity 3-cephem derivative crystals have been produced by such simple process for the first time according to the invention.

Examples of the 3-cephem derivative stated in the invention include, for example, a 3-cephem derivative of the formula (2).

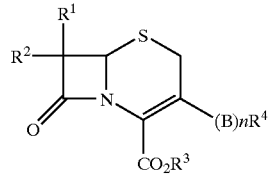

(2)

wherein $R^1$ and $R^2$ are the same or different and each of them is a hydrogen atom, a halogen atom, a group —$OR^5$ (wherein $R^5$ is a lower alkyl group, an aryl group or a benzyl group, each optionally having a substituent), an amino group optionally having a substituent or a protected amino group, $R^3$ is a hydrogen atom or a carboxylic acid-protecting group, B is a lower alkylene group, or a lower alkenylene group, n is 0 or 1, $R^4$ is a hydrogen atom, a hydroxyl group, a halogen atom, a formyl group, a tertiary amino group optionally having a cyclic structure by itself, a group —$OR^5$ ($R^5$ is as defined above), a group —$SR^6$ ($R^6$ is a lower alkyl group, a lower alkenyl group, a benzyl group, an aryl group or a heterocyclic hydrocarbon group, each optionally having a substituent), a group —$OSO_2R^7$ ($R^7$ is a halogen atom, or a lower alkyl group or an aryl group, each optionally having a substituent).

In the present invention, carbon dioxide in a supercritical or subcritical state is incorporated under an increased pressure, into a solution of an amorphous powder or oil of 3-cephem derivative in a good solvent, or into the reaction mixture in the procedure for producing a 3-cephem derivative, whereby a 3-cephem derivative in crystalline form can be produced.

Optionally in the invention, the reaction mixture in the procedure for producing a 3-cephem derivative is incorporated into carbon dioxide in a supercritical or subcritical state under an increased pressure, whereby a 3-cephem derivative in crystalline form can be produced.

Stated more specifically, the groups described in the instant specification include the following. Unless specially indicated, the halogen atom is fluorine, chlorine, bromine or iodine. The lower alkyl group includes, for example, methyl, ethyl, propyl, isopropyl, butyl, isobutyl, sec-butyl, tert-butyl and like straight-chain or branched-chain alkyl groups having 1 to 4 carbon atoms. The lower alkylene group includes, for example, methylene, ethylene, propylene, tetramethylene and like straight-chain or branched-chain alkylene groups having 1 to 4 carbon atoms. The lower alkenyl group includes vinyl, propenyl, butenyl and like straight-chain or branched-chain alkenyl groups having 2 to 4 carbon atoms. The lower alkenylene group includes vinylene, propenylene, butenylene and like straight-chain or branched-chain alkenylene groups having 2 to 4 carbon atoms. The aryl group includes, for example, phenyl and naphthyl. The heterocyclic hydrocarbon group includes, for example, thienyl, furyl, piperidyl, pyridyl, imidazolyl, benzotriazolyl, tetrazolyl, thiazolyl, benzothiazolyl, thiadiazolyl and like 4- to 6-membered cyclic groups having 1 to 4 hetero-atoms and groups having their salts.

The amino group optionally having a substituent which is represented by $R^1$ and $R^2$ includes amino, amino which is substituted with lower alkyl, a group —CO—CH(X)Y or a group —CO—C(=Q-Z)Y.

In the above, X is a hydrogen atom, an amino group or an amino group which is substituted with a group —COA (wherein A is a heterocyclic hydrocarbon group optionally having a substituent), Y is a cyclohexadienyl group, a phenyl group optionally having a substituent or a heterocyclic hydrocarbon group optionally having a substituent, Z is a lower alkyl group, a hydroxyl group or a group —$OR^5$, and Q is a methylidyne group or a nitrogen atom.

Examples of the substituent of the lower alkyl group in $R^5$ to $R^7$ are halogen, carboxyl, hydroxyl, nitro, cyano, amino, mercapto, aryl, alkylthio and arylthio. Examples of the substituent of the heterocyclic hydrocarbon group in $R^6$ are lower alkyl, halogen, carboxyl, hydroxyl, nitro, cyano, amino, mercapto, aryl, alkylthio and arylthio.

Exemplary of the protected amino represented by $R^1$ are amido groups such as phenoxyacetamido, p-methylphenoxyacetamido, p-methoxyphenoxyacetamido, p-chlorophenoxyacetamido, p-bromophenoxyacetamido, phenylacetamido, p-methylphenylacetamido, p-methoxyphenylacetamido, p-chlorophenylacetamido, p-bromophenylacetamido, phenylmonochloroacetamido, phenyldichloroacetamido, phenylhydroxyacetamido, thienylacetamido, phenylacetoxyacetamido, α-oxophenylacetamido, benzamido, p-methylbenzamido, p-methoxybenzamido, p-chlorobenzamido, p-bromobenzamido, phenylglycylamido, phenylglycylamido having protected amino, p-hydroxyphenylglycylamido, p-hydroxyphenylglycylamido having protected amino and/or protected hydroxyl, etc.; imido groups such as phthalimido, nitrophthalimido, etc., in addition to the groups disclosed in Theodora W. Greene, 1981, "Protective Groups in Organic Synthesis" (hereinafter referred to merely as the "literature"), Chap. 7 (pp. 218 287). Examples of protective groups for the amino of phenylglycylamido group and p-hydroxyphenylglycylamido group are those disclosed in the literature, Chap. 7 (pp. 218 287). Examples of protective groups for the hydroxyl of p-hydroxyphenylglycylamido group are those disclosed in the literature, Chap.2 (pp. 10 72).

Further, also are included groups of the formula (3)

(3)

wherein Ri and Rj are the same or different and each of them is a hydrogen atom, lower alkyl group; aryl group or heterocyclic hydrocarbon group, or may bond together to form a cyclic group.

Exemplary of the carboxylic acid protecting group represented by $R^3$ are allyl, benzyl, p-methoxybenzyl, p-nitrobenzyl, diphenylmethyl, trichloromethyl, tert-butyl, and those disclosed in the literature, Chap. 5 (pp. 152 192).

Examples of the tertiary amino group optionally having a cyclic structure by itself which is represented by $R^4$ are dimethylamino, diethylamino, methylethylamino, dicyclopropylamino, morpholino, pyrrodinyl, piperazinyl, imidazolyl and tetrazolyl.

Examples of good solvents used in the invention are lower alkyl alcohols such as methanol, ethanol and propanol, lower alkyl esters of lower alkyl carboxylic acids such as methyl formate, ethyl formate, propyl formate, butyl formate, methyl acetate, ethyl acetate, propyl acetate, butyl acetate, methyl propionate and ethyl propionate, ketones such as acetone, methyl ethyl ketone, methyl propyl ketone, methyl butyl ketone, methyl isobutyl ketone and diethyl ketone, ethers such as diethyl ether, ethyl propyl ether, ethyl butyl ether, dipropyl ether, diisopropyl ether, dibutyl ether, methyl cellosolve and dimethoxyethane, cyclic ethers such as tetrahydrofuran, dioxane and dioxolan, nitriles such as acetonitrile, propionitrile, butyronitrile, isobutyronitrile and valeronitrile, aromatic hydrocarbons such as benzene, toluene, xylene, chlorobenzene and anisole, hydrocarbon halides such as dichloromethane, chloroform, dichloroethane, trichloroethane, dibromoethane, propylene dichloride, carbon tetrachloride and freons, aliphatic hydrocarbons such as pentane, hexane, heptane and octane, cycloalkanes such as cyclopentane, cyclohexane, cycloheptane and cyclooctane, amides such as dimethylformamide and dimethylacetamide, dialkylsulfoxides such as dimethylsulfoxide. The term "good solvent" used herein means a solvent capable of dissolving the 3-cephem derivative of the invention. These organic solvents can be used either alone or in combination. The solvent is used in an amount of about 0.1 liter to about 200 liters, preferably about 1 liter to about 100 liters, per kilogram of the compound of the formula (1).

The organic solvent may contain water when so required. The proportion of water contained in the solvent is 0.1 to 20 vol. %, preferably 0.5 to 10 vol. %, based on the organic solvent used.

The critical point of carbon dioxide has a temperature of 31° C. and a pressure of 7.3 MPa. The carbon dioxide having a temperature and a pressure beyond the critical point is termed supercritical carbon dioxide, whereas the carbon dioxide having a temperature (about 20 to 30° C.) and a pressure (about 6 to 7.2 MPa) slightly below the critical point is termed subcritical carbon dioxide.

The carbon dioxide in a supercritical or subcritical state which is used in the present invention has a pressure in the range of about 3 to about 40 MPa, preferably about 6 to about 30 MPa. The temperature for crystallization is in the range of about 5 to about 70° C., preferably about 20 to about 50° C., although variable depending on the pressure.

The proportions (V/V) of carbon dioxide in a supercritical or subcritical state and the organic solvent are approximately 10:90 to 99:1, preferably approximately 30:70 to 90:10, although variable depending on the temperature and pressure of the organic solvent, substrate and carbon dioxide used at the time of crystallization.

The supercritical or subcritical carbon dioxide used can be easily recovered by reducing the pressure so that the carbon dioxide recovered after crystallization, filtration and washing operations and brought again to a supercritical or subcritical state can be used.

In the invention, purification and isolation can be easily performed to give high-purity, highly stable crystals without residual solvent from an amorphous powder or oil of raw material. Further the carbon dioxide used is non-polluting and non-combustible and can be easily recovered and reused only by adjusting the pressure and temperature.

The same organic solvent as the good solvent for dissolving the amorphous powder or oil of 3-cephem derivative may be used as the solvent for dissolving the amorphous powder or oil of 3-cephem derivative in the process for preparing 3-cephem derivative crystals in which crystallization is performed using as a seed crystal the crystals obtained by the crystallization method of the invention using, as a poor solvent, carbon dioxide in a supercritical or subcritical state. These good solvents can be used either alone or in combination. The amount of the organic solvent used is such that the amount of dissolved 3-cephem derivative is brought to super-saturated state or nearly super-saturated state.

It is possible to use, if necessary, a solvent (comparative poor solvent) which is lower in the power of dissolving the 3-cephem derivative than the organic solvent as a good solvent. Examples of such comparative poor solvent are water, diethyl ether, diisopropyl ether, pentane, hexane, heptane and octane. The amount of the poor solvent used is 0.1 to 20 vol. %, preferably 0.5 to 10 vol. %, based on the organic solvent. The amount of the seed crystal used is about 0.1 to about 10% by weight based on the amorphous powder or oil used. It is preferable to carry out the crystallization method of the invention using the seed crystal at a temperature of −10 to 30° C. By the crystallization method of the invention using the seed crystal, crystals of clathrate compound may be produced depending on a combination of 3-cephem derivative selected and solvent used.

When using the clathrate crystals of the invention comprising the 3-formylcephem compound (1) and dimethylformamide, an antibiotic such as cefixime can be prepared with a purity as high as 95% or more in a high yield of 90% or higher.

In the present invention, X-ray powder diffraction spectrum was determined with use of an apparatus (trade name RAD-IIA, product of Rigaku Co., Ltd.) under the following measuring conditions.

Radiation source: copper radiation of 1.5418 angstrom in wavelength passed through a monochromator
Vessel voltage: 40 KV
Vessel current: 40 mA
Scan angle (2θ): 5 to 60 degrees
Sampling width: 0.020 degree
Scan speed: 3 deg./min.

Among clathrate crystals comprising 3-formylcephem compound (1) and dimethylformamide according to the invention, crystalline solid material characterized by the following X-ray powder diffraction pattern obtained under the same conditions as those mentioned above is preferred.

Spacing of lattice planes (d)
10.87 to 11.71
8.42 to 9.30
6.35 to 6.79
5.64 to 6.24
4.67 to 4.87
4.49 to 4.60
4.38 to 4.48
4.09 to 4.18
3.92 to 3.99
3.83 to 3.91
3.63 to 3.71
3.33 to 3.36

Among clathrate crystals comprising 3-formylcephem compound (1) and dimethylformamide according to the invention, white crystalline solid material characterized by the following X-ray powder diffraction pattern obtained under the same conditions as those mentioned above is preferred.

| Spacing of lattice planes (d) | Relative intensity (I/Io) |
|---|---|
| 10.87 to 11.71 | 0.61 to 0.67 |
| 8.42 to 9.30 | 0.50 to 0.56 |
| 6.35 to 6.79 | 0.70 to 0.78 |
| 5.64 to 6.24 | 0.32 to 0.36 |
| 4.67 to 4.87 | 0.69 to 0.77 |
| 4.49 to 4.60 | 0.27 to 0.29 |
| 4.38 to 4.48 | 0.41 to 0.45 |
| 4.09 to 4.18 | 0.30 to 0.36 |
| 3.92 to 3.99 | 0.42 to 0.46 |
| 3.83 to 3.91 | 1.00 |
| 3.63 to 3.71 | 0.46 to 0.50 |
| 3.33 to 3.36 | 0.29 to 0.32 |

Examples of clathrate crystals comprising 3-formylcephem compound (1) and dimethylformamide according to the invention include those having the following X-ray powder diffraction pattern obtained under the same conditions as those mentioned above.

| Spacing of lattice planes (d) | Relative intensity (I/Io) |
|---|---|
| 10.87 to 11.71 | 0.61 to 0.67 |
| 8.42 to 9.30 | 0.50 to 0.56 |
| 7.30 to 7.70 | 0.04 to 0.05 |
| 7.20 to 7.00 | 0.19 to 0.21 |
| 6.80 to 6.99 | 0.18 to 0.20 |
| 6.35 to 6.79 | 0.70 to 0.78 |
| 5.64 to 6.24 | 0.32 to 0.36 |
| 5.36 to 5.60 | 0.04 to 0.06 |
| 5.20 to 5.35 | 0.06 to 0.08 |
| 5.09 to 5.19 | 0.09 to 0.11 |
| 4.88 to 5.08 | 0.20 to 0.22 |
| 4.67 to 4.87 | 0.69 to 0.77 |
| 4.49 to 4.60 | 0.27 to 0.29 |
| 4.38 to 4.48 | 0.41 to 0.45 |
| 4.30 to 4.37 | 0.06 to 0.08 |
| 4.19 to 4.28 | 0.08 to 0.10 |
| 4.09 to 4.18 | 0.30 to 0.36 |
| 4.00 to 4.08 | 0.16 to 0.18 |
| 3.92 to 3.99 | 0.42 to 0.46 |
| 3.83 to 3.91 | 1.00 |
| 3.72 to 3.85 | 0.22 to 0.24 |
| 3.63 to 3.71 | 0.46 to 0.50 |
| 3.57 to 3.62 | 0.14 to 0.16 |
| 3.52 to 3.56 | 0.06 to 0.08 |
| 3.45 to 3.51 | 0.11 to 0.13 |
| 3.41 to 3.44 | 0.09 to 0.11 |
| 3.37 to 3.40 | 0.10 to 0.12 |
| 3.33 to 3.36 | 0.29 to 0.32 |
| 3.29 to 3.32 | 0.14 to 0.16 |
| 3.10 to 3.24 | 0.15 to 0.17 |
| 3.01 to 3.07 | 0.14 to 0.16 |
| 2.94 to 3.00 | 0.07 to 0.09 |
| 2.83 to 2.93 | 0.11 to 0.13 |

In the clathrate crystals comprising 3-formylcephem compound (1) and dimethylformamide according to the invention, the proportions of crystals of 3-formylcephem compound (1) and dimethylformamide are properly variable according to the ratio thereof used, amount of supercritical or subcritical carbon dioxide used, temperature, pressure, temperature condition at the time of crystallization and other factors, but their proportions are such that the clathrate crystals contain 1 to 99 mole %, preferably 40 to 90 mole %, of the crystals of 3-formylcephem compound (1).

It can be confirmed from, e.g., integration ratio of 1H-NMR spectrum that the crystals of 3-formylcephem compound (1) according to the invention are clathrate crystals of 3-formylcephem compound (1) and dimethylformamide.

The crystals of 3-formylcephem compound (1) according to the invention can be prepared by dissolving an amorphous powder and/or oil of 3-formylcephem compound (1) in water-containing dimethylformamide and adding supercritical or subcritical carbon dioxide to the solution for crystallization.

The water content of the water-containing dimethylformamide is not specifically limited but is usually 0.2 to 20 vol. %, preferably 1 to 10 vol. %. At least one kind of other organic solvents than dimethylformamide can be used along with dimethylformamide. The organic solvent is not limited insofar as it has high compatibility with dimethylformamide and it does not adversely affect the crystallization reaction. Examples of the organic solvent to be used are diethylformamide, dimethylacetamide and like amide solvents. The proportion of the organic solvent to be used together with dimethylformamide is not specifically limited. The proportion thereof is so determined that 3 vol. % or more, preferably 10 vol. % or more, of dimethylformamide is incorporated.

The crystals of 3-formylcephem compound (1) produced in this manner can be isolated from the reaction system by conventional purification means. For example, cephalosporin crystals precipitated in the reaction system are collected by filtration and dried under atmospheric or reduced pressure preferably at about 25 to about 45° C.

As described above, the crystals of 3-formylcephem compound (1) of the invention can be an intermediate in preparing, e.g. the above-mentioned antibiotic cefixime. Cefixime can be produced as shown in the reaction scheme given below.

The crystals of 3-formylcephem compound (1) according to the invention is reacted with methyltriphenyl phosphonium iodide and sodium carbonate to give p-methoxybenzyl ester of 7-phenylacetamide-3-vinyl-3-cephem-4-carboxylic acid. The ester is treated with phosphorus pentachloride/pyridine and isobutanol is added to thereby eliminate 7-position side chain. The obtained p-methoxybenzyl ester of 7-amino-3-vinyl-3-cephem-4-carboxylic acid is deprotected at 4-position p-methoxybenzyl ester group, giving 7-amino-3-vinyl-3-cephem-4-carboxylic acid. The compound can be made into cefixime by the process described in JP-A-63-20435.

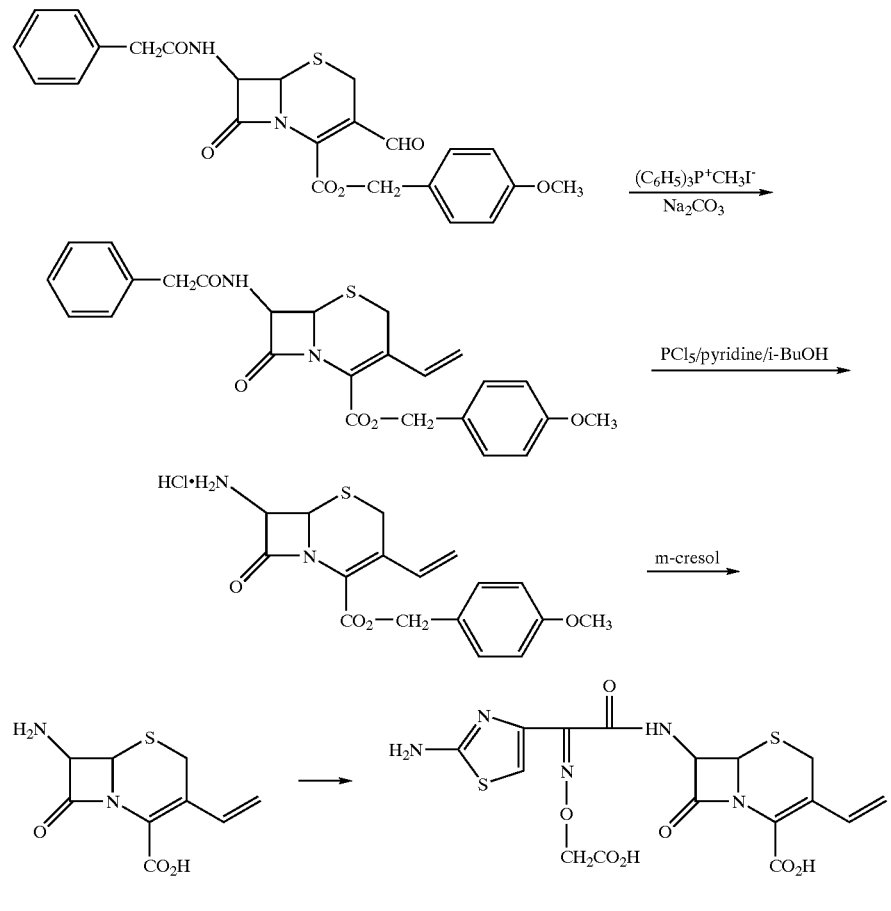

cefixime

BEST MODE OF CARRYING OUT THE INVENTION

Figure 1:
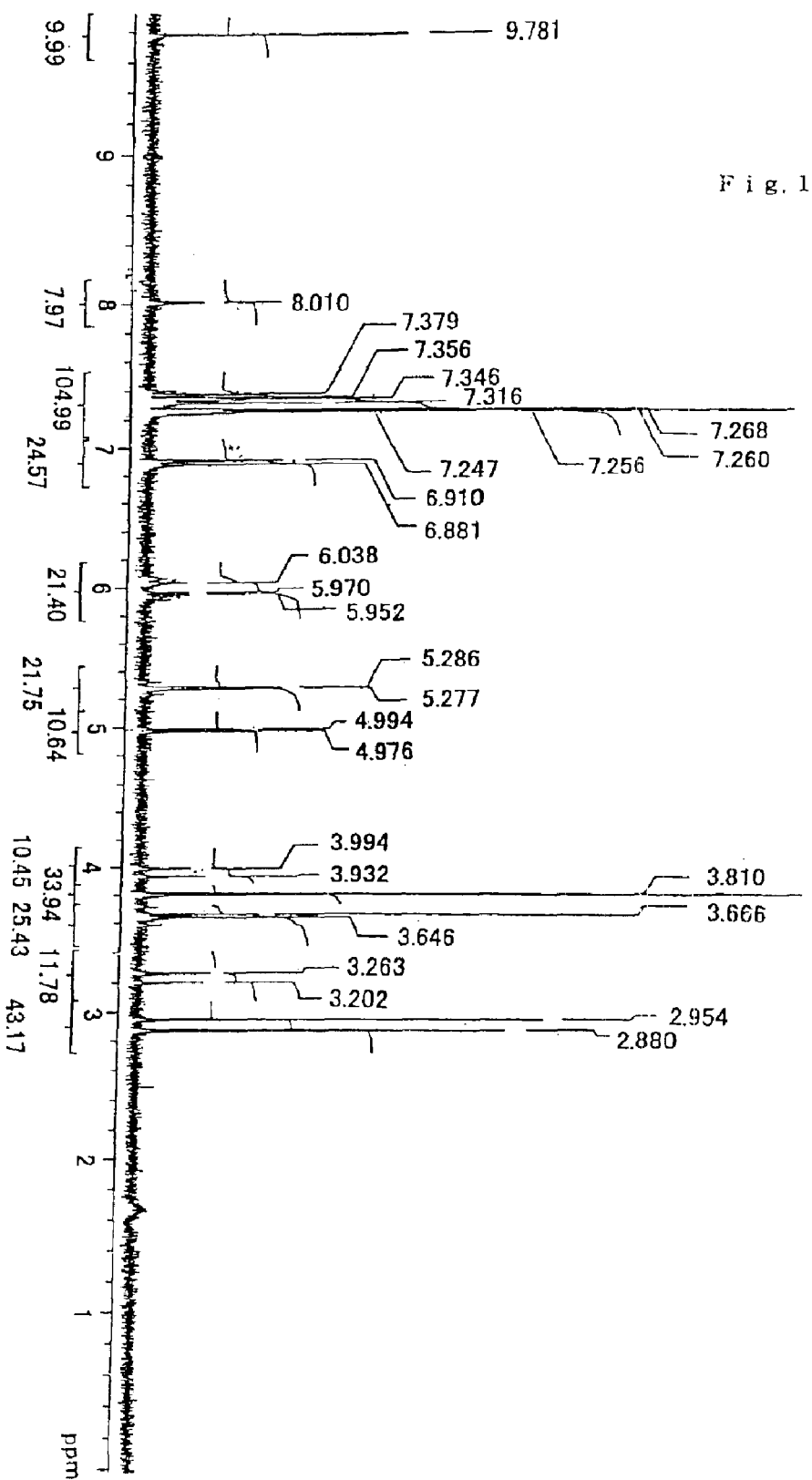
FIG. 1 shows 1H-NMR spectrum of 3-cephem derivative crystals of the invention obtained in Example 1.

The novel crystallization method of the invention will be described below with reference to the following reference examples and examples to which, however, the invention is not limited.

REFERENCE EXAMPLE 1

Isopropyl alcohol (2000 ml) was placed into a 3 liter-eggplant type flask and was cooled to 3° C. Separately a solution of 120 g of an amorphous powder of p-methoxybenzyl ester of 7-phenylacetamide-3-formyl-3-cephem-4-carboxylic acid [3-formylcephem compound (1)] (88% purity) in 120 ml of dimethylformamide was prepared.

The dimethylformamide solution was added dropwise to the sufficiently cooled isopropyl alcohol. The mixture was stirred for 1 hour while holding the internal temperature at 5 to 10° C., whereby a powder of 3-formylcephem compound (1) was precipitated. After completion of aging, the precipitate was filtered. After filtration, the obtained particles were washed with 300 ml of isopropyl alcohol at 5° C.

Drying was conducted under 10 Torr at 45° C. for 12 hours, giving 105.6 g of 3-formylcephem compound (1).

The melting point of the compound was measured but it was not definite. The compound started to decompose to ashing at about 156° C., which reveals that the compound was an amorphous powder (purity 89.0%, yield 89.0%).

EXAMPLE 1

A 500 ml-pressure vessel with a sintered filter was charged with a solution of 120 g of an amorphous powder of 3-formylcephem compound (1) (88% purity) in 120 ml of 2% water-containing dimethylformamide. Then, carbon dioxide was forced into the vessel with stirring up to 15 MPa while holding the internal temperature at 35° C.

After the internal temperature was elevated to 45° C., the mixture was stirred for aging for 30 minutes, whereby crystals were precipitated. After completion of aging, the precipitated crystals were filtered at the same temperature. The obtained particles were washed with 100 g of supercritical carbon dioxide at 35° C., and were degassed, giving 120.8 g of dried crystals (m.p.159.1° C.).

FIG. 1 shows $^1$H-NMR spectrum of obtained crystals [$^1$H-NMR (CDCl$_3$) δppm]. As apparent from FIG. 1, the main peaks of the crystals corresponded to those of 3-formylcephem compound (1). The NMR spectrum had three peaks derived from dimethylformamide, i.e. 2.880 (s, 3H), 2.954 (s, 3H) and 8.010 (s, 1H). It was confirmed from, e.g., integration ratio of NMR spectrum that the crystals are clathrate crystals (purity 95%, yield 94.0%) containing 50 mole % of 3-formylcephem compound (1) and 50 mole % of dimethylformamide.

X-ray powder diffraction pattern of the clathrate crystals obtained with copper radiation (λ=1.5418 Å) passed through a monochromator are as follows.

| d | 1/I |
| --- | --- |
| 11.4 | 0.64 |
| 8.86 | 0.53 |
| 7.51 | 0.04 |
| 7.12 | 0.20 |
| 6.98 | 0.19 |
| 6.67 | 0.74 |
| 5.95 | 0.34 |
| 5.47 | 0.05 |
| 5.33 | 0.07 |
| 5.14 | 0.10 |
| 4.94 | 0.21 |
| 4.80 | 0.73 |
| 4.53 | 0.28 |
| 4.44 | 0.43 |
| 4.35 | 0.07 |
| 4.23 | 0.09 |
| 4.15 | 0.32 |
| 4.04 | 0.17 |
| 3.95 | 0.44 |
| 3.89 | 1.00 |
| 3.80 | 0.23 |
| 3.69 | 0.48 |
| 3.60 | 0.15 |
| 3.55 | 0.07 |
| 3.50 | 0.12 |
| 3.43 | 0.10 |
| 3.39 | 0.11 |
| 3.35 | 0.30 |
| 3.33 | 0.15 |
| 3.17 | 0.16 |
| 3.05 | 0.15 |
| 2.97 | 0.08 |
| 2.88 | 0.12 |

EXAMPLE 2

A 500 ml-pressure vessel with a sintered filter was charged with a solution of 120 g of an oil of diphenylmethyl ester of 7-phenylacetamide-3-hydroxy-3-cephem-4-carboxylic acid (87% purity) in 120 ml of methylene chloride. Then, carbon dioxide was forced into the vessel with stirring up to 15 MPa while holding the internal temperature at 20° C. Then the mixture was stirred for aging for 30 minutes while the temperature and pressure were held, whereby diphenylmethyl ester of 7-phenylacetamide-3-hydroxy-3-cephem-4-carboxylic acid was precipitated as crystals. After completion of aging, the precipitated crystals were filtered at the same temperature. The obtained particles were washed with 100 g of supercritical carbon dioxide at 35° C., and were degassed, whereby 109.9 g of diphenylmethyl ester of 7-phenylacetamide-3-hydroxy-3-cephem-4-carboxylic acid (purity 95%, yield 100%) was obtained as a crystalline powder having a definite melting point (m.p.176.5° C.).

EXAMPLE 3

Carbon dioxide was forced into a 500 ml-pressure vessel with a sintered filter up to 15 MPa. Then, a solution of 120 g of an oil of diphenylmethyl ester of 7-phenylacetamide-3-hydroxy-3-cephem-4-carboxylic acid (87% purity) in 120 ml of dimethylformamide was forced into the vessel by a high pressure pump while holding the internal temperature at 25° C. Immediately thereafter, diphenylmethyl ester of 7-phenylacetamide-3-hydroxy-3-cephem-4-carboxylic acid was precipitated as crystals. Then, after the precipitated crystals were filtered at the same temperature, the obtained particles were washed with 100 g of subcritical carbon dioxide at 25° C., and were degassed, whereby 109.9 g of dried diphenylmethyl ester of 7-phenylacetamide-3-hydroxy-3-cephem-4-carboxylic acid (purity 95%, yield 100%) was obtained as a crystalline powder having a definite melting point (m.p.176.5° C.).

EXAMPLES 4 TO 8

Using the 3-cephem derivative compounds in the form of amorphous powder or oil shown in Table 1, and using the reaction mixture after completion of reaction for synthesis of the compounds, crystallization was carried out with carbon dioxide as a poor solvent, giving the contemplated crystalline powder. The results of the reaction are shown in Table 1.

TABLE 1

| Example | 4 | 5 | 6 | 7 | 8 |
|---|---|---|---|---|---|
| Substrate | *A | *B | *C | *D | *E |
| Solvent | DX | DMF | MDC | DEF | DMF |
|  | 120 ml | 120 ml | 120 ml | 120 ml | 83.7 g |
| Crystallization temperature (° C.) | 25 | 35 | 20 | 20 | 35 |
| Condition | Super-critical | Super-critical | Sub-critical | Sub-critical | Super-critical |
| Crystallization pressure (MPa) | 9 | 30 | 6 | 6 | 20 |
| Crystallization time (min) | 10 | 30 | 60 | 30 | 10 |
| Weight (g) | 13.4 | 104.3 | 109.9 | 99.1 | 13.4 |
| Purity (%) | 98 | 96 | 95 | 93 | 98 |
| Yield (%) | 97 | 100 | 100 | 96 | 97 |
| Melting point (° C.) | 176.4 | 157.0 | 176.5 | 196.5 | 176.4 |

Substrate
*A: 20 g of oil of p-methoxybenzyl ester of 7-phenylacetamide-3-chloromethyl-3-cephem-4-carboxylic acid (purity 68%)
*B: 120 g of oil of diphenylmethyl ester of 7-phenylacetamide-3-chloromethyl-3-cephem-4-carboxylic acid (purity 80%)
*C: 120 g of oil of diphenylmethyl ester of 7-phenylacetamide-3-hydroxy-3-cephem-4-carboxylic acid (purity 87%)
*D: 120 g of oil of diphenylmethyl ester of 7-phenylacetamide-3-chloro-3-cephem-4-carboxylic acid (purity 80%)
*E: 120 ml of reaction mixture which, after synthetic reaction, contains 18.6 g of p-methoxybenzyl ester of 7-phenylacetamide-3-chloromethyl-3-cephem-4-carboxylic acid, 12.6 g of inorganic compound as impurities, and 4.9 g of organic compound as impurities.
Solvent
DX: 1,4-Dioxane
DMF: N,N-Dimethylformamide
MDC: Dichloromethane
DEF: N,N-Diethylformamide

EXAMPLE 9

A 1.2 g quantity of amorphous powder of 3-formylcephem compound (1) (purity 80%) was dissolved in 4 ml of dimethylformamide at room temperature. To the solution was added dropwise 0.4 ml of water with stirring. The mixture was stirred with ice cooling for 20 minutes. Then 2 to 3 mg of the clathrate compound crystals obtained in Example 1 was added as a seed crystal, followed by stirring. In about 10 minutes, crystals began to separate out.

Further, stirring was conducted with ice cooling for about 1 hour. Then, the mixture was filtered and washed with diethyl ether. The obtained mixture was dried under reduced pressure, whereby 0.99 g (purity 95%, yield 84.5%) of a clathrate compound comprising 3-formylcephem compound (1) and dimethylformamide was obtained as a crystalline powder having a definite melting point (m.p.159.1° C.).

REFERENCE EXAMPLE 2

The crystalline 3-formylcephem compound (1) obtained according to the invention is an important intermediate of cefixime or the like.

The clathrate compound comprising crystalline 3-formylcephem compound (1) and dimethylformamide obtained in Example 1 was reacted with methyltriphenyl phosphonium iodide and sodium carbonate to produce p-methoxybenzyl ester of 7-phenylacetamide-3-vinyl-3-cephem-4-carboxylic acid. The obtained ester was treated with phosphorus pentachloride/pyridine. Then isobutanol was added to give p-methoxybenzyl ester hydrochloride of 7-amino-3-vinyl-3-cephem-4-carboxylic acid. Phenol was added to the mixture and the mixture was reacted at 45° C. for 1 hour, giving 7-amino-3-vinyl-3-cephem-4-carboxylic acid. The obtained compound can be made into cefixime by the process disclosed in JP-A-63-20435.

TEST EXAMPLE 1

Stability Test

Used were 100 g of clathrate crystals comprising 3-formylcephem compound (1) and dimethylformamide prepared in Example 1 and 100 g of 3-formylcephem compound (1) prepared in Reference Example 1 (amorphous product). They were stored in a thermostatic chamber at 20 to 25° C. and in a refrigerator at 3 to 5° C. for a specified time to determine a factor of decomposition by high performance liquid chromatorgraphy (HPLC). The results are shown in Table 2. It is clear from the table that the cephalosporin crystals of the invention scarcely causes decomposition and are excellent in stability.

TABLE 2

| | temperature (° C.) | time (day) | Decomposition rate (%) |
|---|---|---|---|
| crystal | 20 to 25 | 14 | 2 |
| amorphous product | 20 to 25 | 14 | 59 |
| crystal | 3 to 5 | 48 | 0 |
| amorphous product | 3 to 5 | 48 | 13 |

INDUSTRIAL APPLICABILITY

The present invention has the following advantages over the prior art.
1) The desired crystalline product can be prepared from an amorphous powder or oil of the raw material.
2) A higher purity product can be produced by single crystallization operation.
3) The desired product can be prepared merely by removal of carbon dioxide and heat energy for drying is inexpensive.
4) Due to high diffusibility of supercritical fluid, the contemplated component can be quickly crystallized from the tar-like viscous reaction mixture of raw material.
5) Carbon dioxide is non-polluting, non-combustible and inexpensive and can be easily recycled.
6) Once crystalline 3-cephem derivative is obtained by a crystallization method using carbon dioxide in a supercritical or subcritical state as a poor solvent, crystals of 3-cephem derivative can be easily prepared from an amorphous powder or oil of 3-cephem derivative without use of carbon dioxide in a supercritical or subcritical state.
7) According to the invention, it is possible to prepare highly stabilized, although highly active in terms of reaction, crystals of p-methoxybenzyl ester of 7-phenylacetamide-3-formyl-3-cephem-4-carboxylic acid.

What is claimed is:

1. A clathrate compound comprising p-methoxybenzyl ester of 7-phenylacetamide-3-formyl-3-cephem-4-carboxcylic acid and dimethylformamide in crystalline form.

2. A clathrate compound as defined in claim 1 which has peaks at the following spacing of lattice planes (d) in the X-ray powder diffraction pattern obtained under copper radiation of 1.5418 angstrom in wavelength passed through a monochromator:

spacing of lattice planes (d)
10.87 to 11.71
8.42 to 9.30
6.35 to 6.79
5.64 to 6.24
4.67 to 4.87
4.49 to 4.60
4.38 to 4.48
4.09 to 4.18
3.92 to 3.99
3.83 to 3.91
3.63 to 3.71
3.33 to 3.36.

* * * * *